(12) United States Patent
Hagihara et al.

(10) Patent No.: US 8,193,358 B2
(45) Date of Patent: Jun. 5, 2012

(54) PROCESS FOR PRODUCING HIGH-PURITY PRASUGREL AND ACID ADDITION SALT THEREOF

(75) Inventors: Masahiko Hagihara, Yamaguchi (JP); Hiroyuki Miyata, Yamaguchi (JP); Yukinori Wada, Yamaguchi (JP); Naoyuki Yokota, Yamaguchi (JP)

(73) Assignees: Daiichi Sankyo Company, Limited, Tokyo (JP); Ube Industries, Ltd., Yamaguchi (JP)

( * ) Notice: Subject to any disclaimer, the term of this patent is extended or adjusted under 35 U.S.C. 154(b) by 577 days.

(21) Appl. No.: 12/225,762

(22) PCT Filed: Apr. 6, 2007

(86) PCT No.: PCT/JP2007/057785
§ 371 (c)(1),
(2), (4) Date: Nov. 14, 2008

(87) PCT Pub. No.: WO2007/114526
PCT Pub. Date: Oct. 11, 2007

(65) Prior Publication Data
US 2009/0203729 A1    Aug. 13, 2009

(30) Foreign Application Priority Data

Apr. 6, 2006 (JP) ................................ 2006-105555
Mar. 2, 2007 (JP) ................................ 2007-053094

(51) Int. Cl.
*C07D 495/04* (2006.01)
(52) U.S. Cl. .......................................................... 546/114
(58) Field of Classification Search .................... 546/114
See application file for complete search history.

(56) References Cited

U.S. PATENT DOCUMENTS

| 5,288,726 A | 2/1994 | Koike et al. |
| 5,436,242 A | 7/1995 | Koike et al. |
| 5,874,581 A | 2/1999 | Ataka et al. |
| 6,693,115 B2 | 2/2004 | Asai et al. |
| 2003/0134872 A1 | 7/2003 | Asai et al. |

FOREIGN PATENT DOCUMENTS

| GB | 2469883 A | 11/2010 |
| WO | WO 2009/129983 A1 | 10/2009 |
| WO | WO 01/04392 A1 | 1/2011 |

OTHER PUBLICATIONS

International Preliminary Report on Patentability dated Apr. 6, 2006 in PCT/JP2007/057785 (English-language version) (7 pages).
Supplementary European Search Report in Application No. 07741221.1 dated Jan. 7, 2010 (English-language version) (9 pages).
Written Opinion of International Search Authority in PCT/JP2007/057785 dated Jun. 19, 2007 (Japanese-language version) (5 pages).
Third Party Observation in European Application No. 07741221.1 dated Apr. 6, 2011 (8 pages).
Third Party Observation in Euorpean Application No. 07741221.1 dated Apr. 7, 2010 (3 pages).
Doggrell S A et al., "CS-747 and R-99224 Platelet Antiaggregatory P2T Antagonist," *Drugs of the Future, Prous Science, ES*, vol. 26, No. 9, Sep. 1, 2001, pp. 835-840.
English-language summary of Colombian Oppositions.
The first Examination Report issued on behalf of the Intellectual Property Office of Singapore by Letter of Oct. 30, 2009.
An English translation of the first Examination Report issued by the Russian Patent Office dated Mar. 17, 2010.
The first Examination Report issued by the Australian Patent Office dated Jun. 11, 2010.
The first Examination Report issued by the Canadian Intellectual Property Office dated Jan. 20, 2011.
The first Examination Report issued by the Intellectual Property Office of New Zealand dated May 14, 2010.
An English translation of the first Office Action issued by the Chinese Patent Office received by letter dated Nov. 15, 2010.
European Patent Office action dated Jul. 5, 2011.
Australian Examiner's report dated Jul. 4, 2011.

*Primary Examiner* — Patricia Morris
(74) *Attorney, Agent, or Firm* — Holtz, Holtz, Goodman & Chick, P.C.

(57) ABSTRACT

The present invention is directed to providing prasugrel hydrochloride or the like with a reduced content of OXTP. A method for producing prasugrel hydrochloride with a reduced content of OXTP, comprising dissolving free prasugrel containing OXTP in an inert solvent and adding hydrochloric acid optionally dropwise to the solution for reaction is also provided.

2 Claims, 2 Drawing Sheets

[Figure 1]
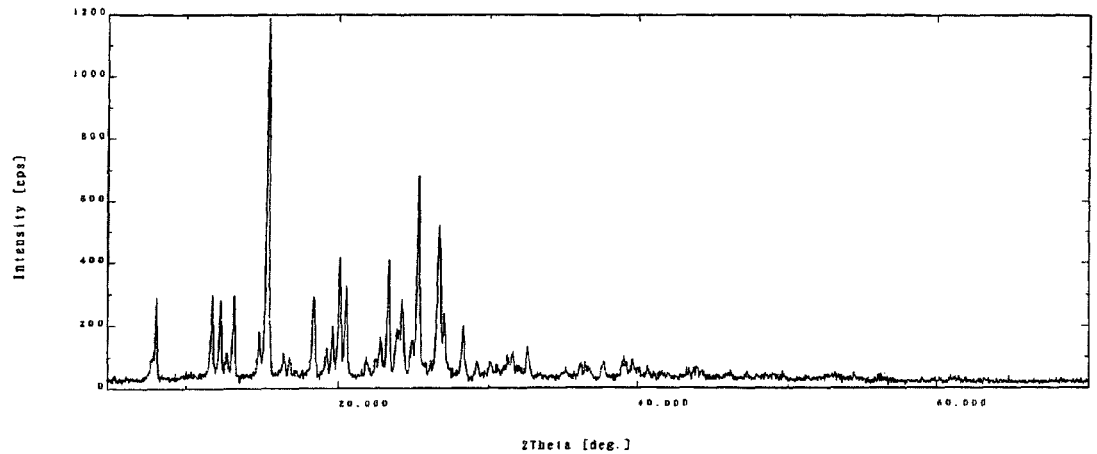
[Figure 2]
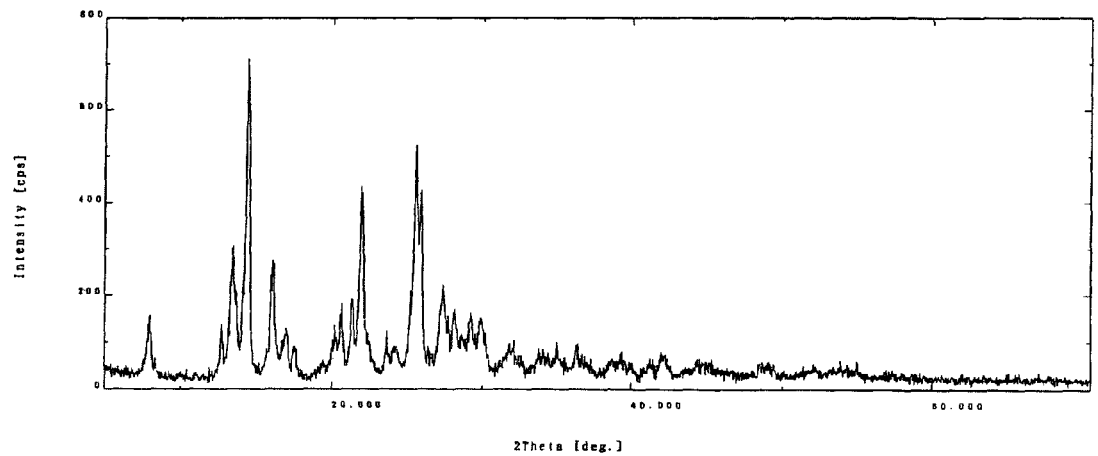
[Figure 3]
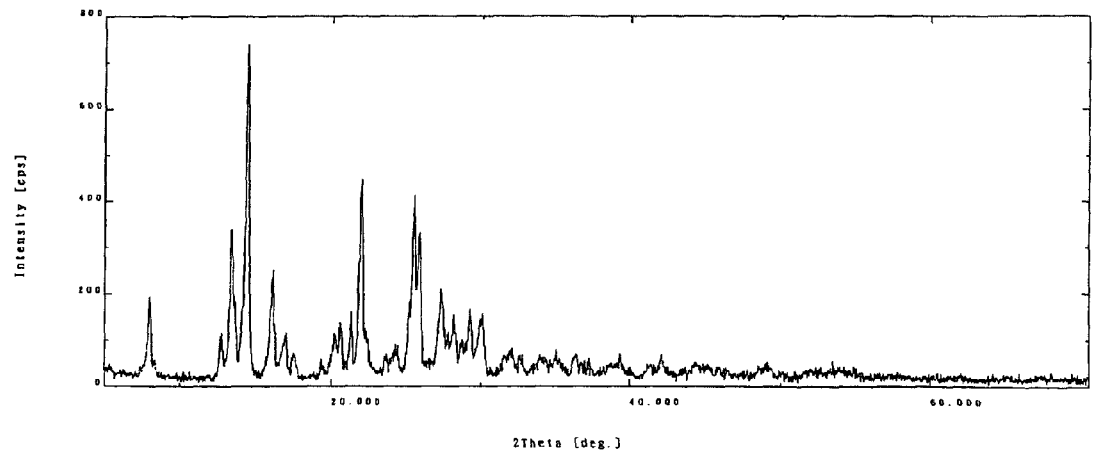

[Figure 4]
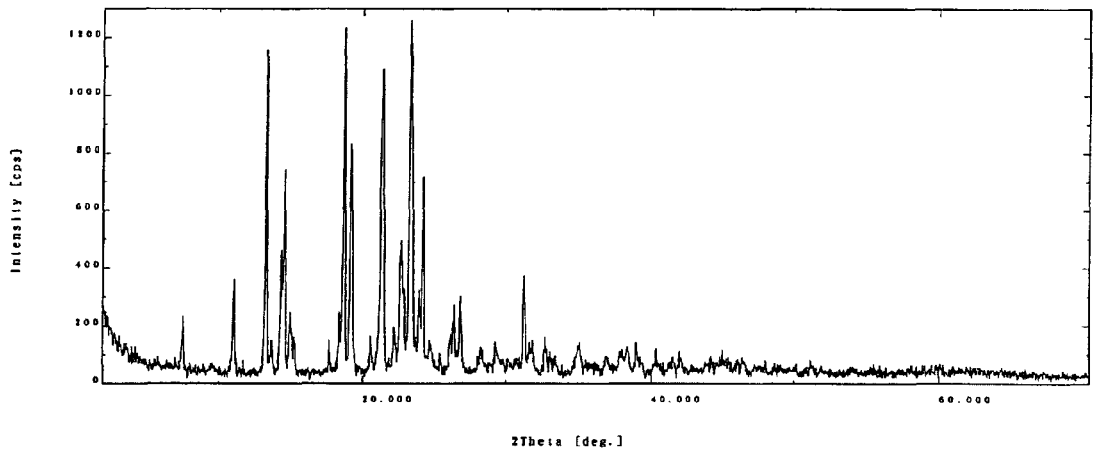
[Figure 5]
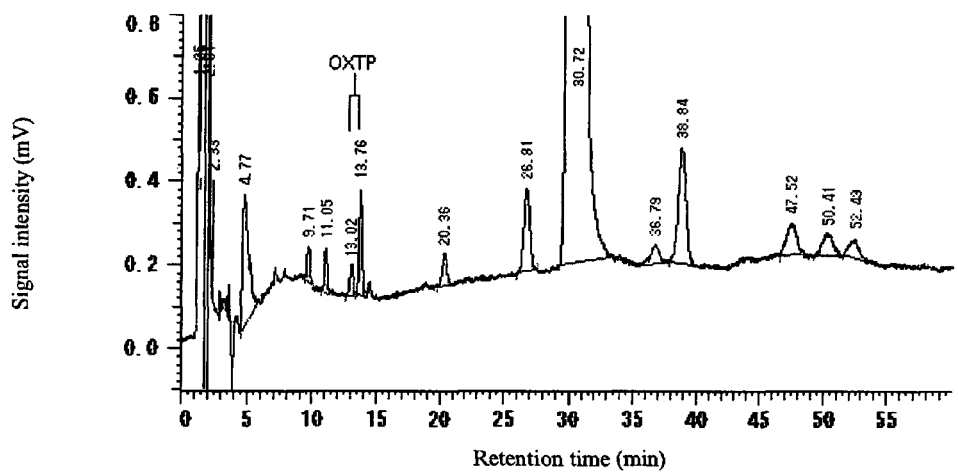
[Figure 6]
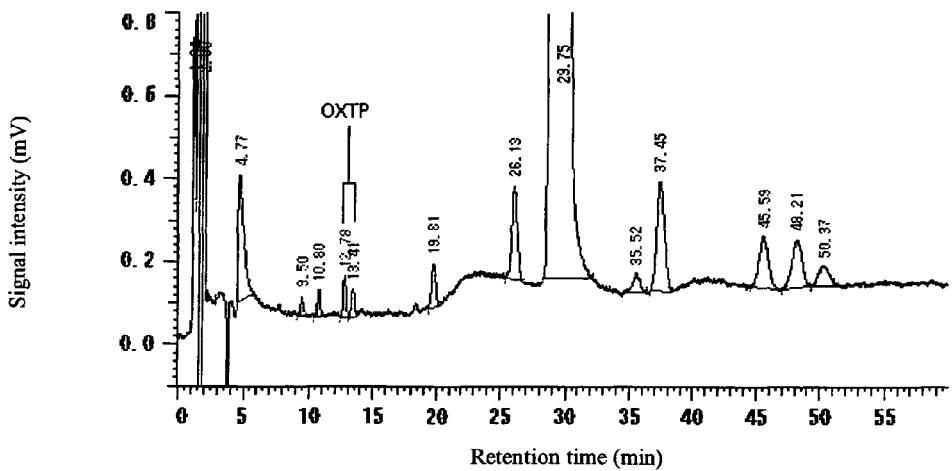

PROCESS FOR PRODUCING HIGH-PURITY PRASUGREL AND ACID ADDITION SALT THEREOF

TECHNICAL FIELD

The present invention relates to a method for producing high-purity prasugrel or an acid addition salt thereof.

BACKGROUND ART

The compound having the formula:

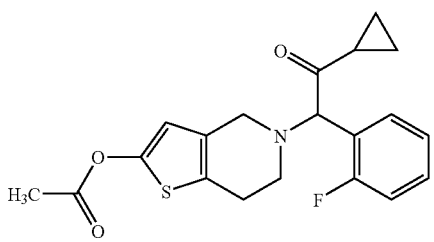

is known as prasugrel. Prasugrel and pharmacologically acceptable salts thereof are known to have a platelet aggregation-inhibiting action and are useful as an active ingredient of a medicine (particularly, an antithrombotic or anti-embolic agent) (JP06-41139 or JP2002-145883). However, the use of prasugrel or a pharmacologically acceptable salt thereof as a medicine has required a technique for producing the prasugrel or a pharmacologically acceptable salt thereof at a high purity.

WO96/11203 describes a method for producing prasugrel or a pharmacologically acceptable salt thereof. In addition, JP2002-145883 describes a method for producing prasugrel hydrochloride or maleate, which involves reacting an acid with free prasugrel. However, neither of these patent documents describes a method for decreasing the by-product OXTP.

Patent Document 1: JP06-41139
Patent Document 2: JP2002-145883
Patent Document 3: WO96/11203

DISCLOSURE OF THE INVENTION

Problems to be Solved by the Invention

An object of the present invention is to provide a method for producing high-purity prasugrel or an acid addition salt thereof by reducing the content of by-products such as OXTP.

Means to Solve the Problems

As a result of intensive studies on a method for producing high-purity prasugrel or the hydrochloride thereof in which the content of impurities such as the by-product OXTP is reduced, the present inventors have found that an acid can be reacted with free prasugrel containing OXTP to make an acid addition salt to reduce the content of the by-product OXTP in the resultant prasugrel hydrochloride to produce high-purity prasugrel hydrochloride. The present inventors have also found that the recrystallization of free prasugrel containing OXTP can reduce the content of the by-product OXTP in the resultant free prasugrel to produce high-purity free prasugrel. Thereby, the present invention has been accomplished.

According to the present invention, the peak of OXTP (the substance with a retention time of 13.02 or 13.76 minutes in FIG. 5 or the substance with a retention time of 12.78 or 13.41 minutes in FIG. 6) in liquid chromatography was greatly reduced compared to the peak of each analogous substance in prasugrel and an acid addition salt thereof (for example, the analogous substance with a retention time of 26.81, 36.79, 38.84 or 52.49 minutes in FIG. 5 or the analogous substance with a retention time of 26.13, 35.52, 37.45 or 50.37 minutes in FIG. 6) in the chromatography.

The present invention provides a method for producing high-purity prasugrel or an acid addition salt thereof (particularly, free prasugrel or the hydrochloride thereof) in each of which the content of OXTP is reduced; high-purity prasugrel or an acid addition salt thereof (particularly, free prasugrel or the hydrochloride thereof) obtained by the production method; a pharmaceutical composition (particularly, a prophylactic or therapeutic agent for diseases caused by thrombus or embolus) containing the high-purity prasugrel or an acid addition salt thereof (particularly, free prasugrel or the hydrochloride thereof) as an active ingredient; use of the high-purity prasugrel or an acid addition salt thereof (particularly, free prasugrel or the hydrochloride thereof) for the purpose of producing a pharmaceutical composition; and a prophylactic or therapeutic method for diseases (particularly, thrombosis or embolism) which involves administering to warm-blooded animals (particularly, humans) a pharmaceutical composition containing a pharmacologically effective amount of high-purity prasugrel or an acid addition salt thereof (particularly, free prasugrel or the hydrochloride thereof).

The present invention is as follows:

(1) A method for producing prasugrel hydrochloride represented by the formula:

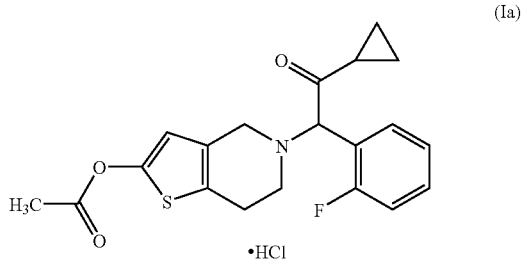

with a reduced content of OXTP, comprising dissolving free prasugrel containing OXTP in an inert solvent and adding hydrochloric acid optionally dropwise to the solution for reaction;

(2) A method for producing prasugrel hydrochloride as described in item (1), wherein the inert solvent is acetone;

(3) Prasugrel hydrochloride containing 0.7% or less of OXTP, produced by a production method as described in item (1) or (2);

(4) Prasugrel hydrochloride containing 0.2% or less of OXTP, produced by a production method as described in item (1) or (2);

(5) Prasugrel hydrochloride containing 0.09% or less of OXTP, produced by a production method as described in item (1) or (2);

(6) Prasugrel hydrochloride containing 0.07% or less of OXTP, produced by a production method as described in item (1) or (2);

(7) Prasugrel hydrochloride containing 0.05% or less of OXTP, produced by a production method as described in item (1) or (2);
(8) Prasugrel hydrochloride characterized by containing 0.7% or less of OXTP;
(9) Prasugrel hydrochloride characterized by containing 0.2% or less of OXTP;
(10) Prasugrel hydrochloride characterized by containing 0.09% or less of OXTP;
(11) Prasugrel hydrochloride characterized by containing 0.7% or less of OXTP;
(12) Prasugrel hydrochloride characterized by containing 0.05% or less of OXTP;
(13) A prasugrel hydrochloride as described in any one of items (3) to (12), wherein the prasugrel hydrochloride is a crystal showing main peaks at spacings (d) of 5.7, 4.4, 3.8, 3.5, and 3.3 angstroms in powder X-ray diffraction obtained by irradiation with copper Kα radiation;
(14) A prasugrel hydrochloride as described in any one of items (3) to (12), wherein the prasugrel hydrochloride is a crystal showing main peaks at spacings (d) of 6.6, 6.1, 4.0, 3.5, and 3.4 angstroms in powder X-ray diffraction obtained by irradiation with copper Kα radiation;
(15) A pharmaceutical composition comprising as an active ingredient a prasugrel hydrochloride as described in any one of items (3) to (14);
(16) A prophylactic or therapeutic agent for use in warm-blooded animals for diseases caused by thrombus or embolus, comprising as an active ingredient a prasugrel hydrochloride as described in any one of items (3) to (14);
(17) A prophylactic or therapeutic agent for use in humans for thrombosis or embolism, comprising as an active ingredient a prasugrel hydrochloride as described in any one of items (3) to (14);
(18) A method for producing free prasugrel with a reduced content of OXTP, comprising recrystallizing free prasugrel containing OXTP;
(19) A production method as described in item (18), wherein the recrystallization uses an ether or a nitrile as a solvent;
(20) A production method as described in item (18), wherein the recrystallization uses acetonitrile as a solvent;
(21) Free prasugrel containing 0.7% or less of OXTP, produced by a production method as described in any one of items (18) to (20);
(22) Free prasugrel containing 0.2% or less of OXTP, produced by a production method as described in any one of items (18) to (20);
(23) Free prasugrel containing 0.09% or less of OXTP, produced by a production method as described in any one of items (18) to (20);
(24) Free prasugrel containing 0.05% or less of OXTP, produced by a production method as described in any one of items (18) to (20);
(25) Free prasugrel containing 0.03% or less of OXTP, produced by a production method as described in any one of items (18) to (20);
(26) Free prasugrel characterized by containing 0.7% or less of OXTP;
(27) Free prasugrel characterized by containing 0.2% or less of OXTP;
(28) Free prasugrel characterized by containing 0.09% or less of OXTP;
(29) Free prasugrel characterized by containing 0.05% or less of OXTP;
(30) Free prasugrel characterized by containing 0.03% or less of OXTP;
(31) Free prasugrel as described in any one of items (21) to (30), wherein the free prasugrel is a crystal showing main peaks at spacings (d) of 6.7, 4.7, 4.6, 4.2, and 3.8 angstroms in powder X-ray diffraction obtained by irradiation with copper Kα radiation;
(32) A pharmaceutical composition comprising as an active ingredient free prasugrel as described in any one of items (21) to (31);
(33) A prophylactic or therapeutic agent for use in warm-blooded animals for diseases caused by thrombus or embolus, comprising as an active ingredient free prasugrel as described in any one of items (21) to (31);
(34) A prophylactic or therapeutic agent for use in humans for thrombosis or embolism, comprising as an active ingredient free prasugrel as described in any one of items (21) to (31);
(35) A method for producing an acid addition salt of prasugrel, characterized in that free prasugrel as described in any one of items (21) to (31) is reacted with an acid in an inert solvent or in the absence of a solvent;
(36) A production method as described in item (35), wherein the acid addition salt is the hydrochloride, maleate, or benzenesulfonate;
(37) An acid addition salt of prasugrel produced by a production method as described in item (35) or (36);
(38) A pharmaceutical composition comprising an acid addition salt as described in item (37) as an active ingredient;
(39) A prophylactic or therapeutic agent for use in warm-blooded animals for diseases caused by thrombus or embolus, comprising as an active ingredient an acid addition salt as described in item (37); and
(40) A prophylactic or therapeutic agent for use in humans for thrombosis or embolism, comprising as an active ingredient an acid addition salt as described in item (37) as an active ingredient.

According to the present invention, the "acid addition salt" can be, for example, an inorganic acid salt such as a sulfate, hydrochloride, nitrate or phosphate; or an organic acid salt such as a trifluoroacetate, maleate, methanesulfonate, benzenesulfonate or p-toluenesulfonate. Preferably, it is a hydrochloride, maleate, or benzenesulfonate, more preferably a hydrochloride.

The prasugrel or an acid addition salt thereof according to the present invention has an asymmetric carbon atom in the molecule; there are stereoisomers having R and S configurations. The stereoisomers and a compound containing these in any proportion are both encompassed within the present invention. The stereoisomers, for example, can be synthesized by using optically resolved raw material compounds or can be obtained by subjecting synthesized prasugrel or an acid addition salt thereof to optical resolution, if desired, using a conventional optical resolution or separation method.

The prasugrel or an acid addition salt thereof according to the present invention may be allowed to stand in the air or recrystallized to absorb water, thereby having an adsorbed water or becoming a hydrate. The water-containing compounds are encompassed within the present invention. In addition, solvates thereof each containing any amount of a solvent are also encompassed within the present invention.

According to the present invention, the prasugrel or an acid addition salt thereof or their-hydrates or solvates can form crystals (crystal polymorphism) having a plurality of different inner structures and physicochemical properties, depending on reaction and crystallization conditions. The crystals and a mixture thereof in any proportion are encompassed within the present invention. Crystalline and amorphous solids thereof may be present as a mixture. A mixture thereof in any proportion is encompassed within the present invention. Specifically, the content of a specific crystal form according to the present invention is preferably 50% or more, more preferably 80% or more, still more preferably 90% or more, particularly preferably 95% or more, most preferably 97% or more.

According to the present invention, a crystal refers to a solid whose inner structure is three-dimensionally composed of a regular repetition of constituent atoms (or a group thereof), and is distinguished from an amorphous solid which does not have such a regular inner structure. Whether or not a solid is a crystal can be examined by a crystallographically known method (for example, powder X-ray crystallography or differential scanning calorimetry). By way of example, a solid is subjected to powder X-ray crystallography using X-rays obtained by irradiation with copper Kα radiation. A solid is determined to be a crystal when distinct peaks are observed in the X-ray diffraction pattern, while a solid is determined to be amorphous when no distinct peaks are observed. A solid is determined to be a crystal whose crystallinity is low when the peaks can be read but are not distinct (e.g., broad). A crystal whose crystallinity is low is encompassed within a crystal of the present invention.

In powder X-ray crystallography using copper Kα radiation, a sample is typically irradiated with copper Kα radiation (in which Kα1 and Kα2 radiations are not separated). An X-ray diffraction pattern can be obtained by analyzing the diffraction derived from Kα radiation, and also by analyzing only the diffraction derived from Kα1 radiation taken out from the diffraction derived from the Kα radiation. According to the present invention, a powder X-ray diffraction pattern obtained by irradiation with Kα radiation encompasses an X-ray diffraction pattern obtained by analyzing the diffraction derived from Kα radiation and an X-ray diffraction pattern obtained by analyzing the diffraction derived from Kα1 radiation, and is preferably an X-ray diffraction pattern obtained by analyzing the diffraction derived from Kα1 radiation.

Crystal A of the prasugrel hydrochloride of the present invention can be, for example, a crystal showing main peaks at spacings (d) of 5.7, 4.4, 3.8, 3.5, and 3.3 angstroms in a powder X-ray diffraction pattern obtained by irradiation with copper Kα radiation as shown in FIG. 1.

Crystal B1 of the prasugrel hydrochloride of the present invention can be, for example, a crystal showing main peaks at spacings (d) of 6.6, 6.1, 4.0, 3.5, and 3.4 angstroms in a powder X-ray diffraction pattern obtained by irradiation with copper Kα radiation as shown in FIG. 2.

Crystal B2 of the prasugrel hydrochloride of the present invention can be, for example, a crystal showing main peaks at spacings (d) of 6.6, 6.1, 4.0, 3.5, and 3.4 angstroms in a powder X-ray diffraction pattern obtained by irradiation with copper Kα radiation as shown in FIG. 3.

A crystal of the free prasugrel of the present invention can be, for example, a crystal showing main peaks at spacings (d) of 6.7, 4.7, 4.6, 4.2, and 3.8 angstroms in a powder X-ray diffraction pattern obtained by irradiation with copper Kα radiation as shown in FIG. 4.

In the powder X-ray diffraction patterns of FIGS. 1 to 4 described below, the ordinate axes represent diffraction intensity (counts/second (cps)) and the horizontal axes represent the diffraction angle 2θ (degrees). The spacing d (angstroms) can be calculated by letting n=1 in the equation: $2d \sin \theta = n\lambda$. In the equation, the Kα radiation wavelength λ is 1.54 angstroms, and the Kα1 radiation wavelength λ is 1.541 angstroms. The identity of crystal forms should be qualified by referring to the pattern of the whole spectrum as needed even when the spacings (d) are slightly different because the position and relative intensity thereof can change somewhat depending on measurement conditions.

According to the present invention, "OXTP" is 5-(α-cyclopropylcarbonyl-2-fluorobenzyl)-2-oxo-2,4,5,6,7,7a-hexahydrothieno[3,2-c]pyridine represented by the formula:

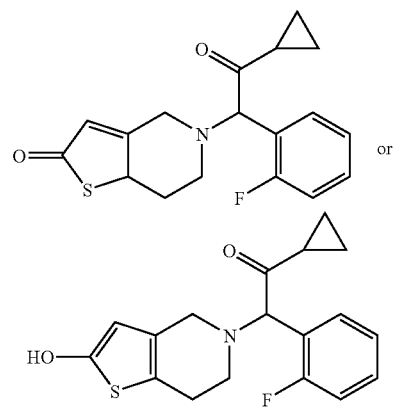

There are keto-enol tautomers for the OXTP according to the present invention. In addition, there is an asymmetric carbon in the OXTP and optical isomers exist based thereon. These isomers and a mixture thereof also fall within the OXTP according to the present invention.

EFFECTS OF THE INVENTION

According to the present invention, there can be provided high-purity prasugrel and an acid addition salt thereof (particularly, free prasugrel and the hydrochloride thereof) in each of which the content of impurities such as the by-product OXTP is reduced.

BEST MODE FOR CARRYING OUT THE INVENTION

Free prasugrel can be produced as a starting material for the present invention by the production method described in WO96/11203.

A method embodying the present invention for producing high-purity prasugrel hydrochloride, free prasugrel, and an acid addition salt thereof is as follows.

Process for Producing High-Purity Prasugrel Hydrochloride from Free Prasugrel

This process is a process which involves dissolving free prasugrel in an inert solvent, adding hydrochloric acid optionally dropwise thereto, and, if necessary, adding a seed crystal for reaction to produce high-purity prasugrel hydrochloride.

In this process, the adding of hydrochloric acid optionally dropwise may be carried out by adding the acid dropwise or adding the acid at one time or in two to several divided portions. The solvent used in this process is not particularly limited, provided that it dissolves the starting material to a degree and does not inhibit the reaction. The solvent can be, for example, an aliphatic hydrocarbon such as hexane, cyclohexane, heptane, ligroin, or petroleum ether; an aromatic hydrocarbon such as benzene, toluene, or xylene; a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or diethylene glycol dimethyl ether; a ketone such as acetone, methyl ethyl ketone, or diethyl ketone; an ester such as ethyl acetate, propyl acetate, or butyl acetate; a carboxylic acid such as acetic acid or propionic acid; or a nitrile such as acetonitrile or propionitrile. Preferably, it is an ether, a ketone, an ester, a carboxylic acid, or a nitrile, more preferably tetrahydrofuran, dioxane, acetone, methyl ethyl ketone, ethyl acetate, acetic acid, or acetonitrile, particularly preferably tetrahydrofuran, dioxane, acetic acid, or acetone, most preferably acetone.

The reaction temperature in the process varies depending on the reagent, solvent, or the like. However, it is typically −20° C. to 100° C., preferably 0° C. to 70° C., more preferably 30° C. to 60° C., most preferably 40° C. to 55° C.

The reaction time in the process varies depending on the reagent, solvent, reaction temperature, or the like. However, it is typically 5 minutes to 10 hours, preferably 10 minutes to 5 hours.

A preferred aspect of the process is a method which involves dissolving free prasugrel in acetone, adding dropwise half of the necessary amount (typically, equimolar to the thienopyridine form) of concentrated hydrochloric acid to the solution at 0° C. to 70° C. (preferably 35° C. to 60° C.) over a period of 2 minutes to 10 minutes, adding, if necessary, a seed crystal for reaction at the same temperature for 30 minutes to 2 hours, and further adding dropwise the remaining necessary amount of concentrated hydrochloric acid over a period of 30 minutes to 2 hours for reaction at 0° C. to 70° C. (preferably 25° C. to 55° C.) for 1 hour to 3 hours.

After the end of the reaction process, the prasugrel hydrochloride of the present invention is collected from the reaction mixture according to a conventional method. For example, the desired compound is obtained by collecting the precipitated crystal by filtration after the end of the reaction or distilling off the solvent after the end of the reaction. The desired compound obtained may be, if necessary, further purified by a conventional method, for example, recrystallization, reprecipitation, or chromatography.

The high-purity prasugrel hydrochloride obtained in the process can be measured for the OXTP content using the following method.

The content of OXTP in the prasugrel hydrochloride is measured by liquid chromatography and expressed in percentage by area (%) in terms of the content of OXTP in free prasugrel.

The content of OXTP in the high-purity prasugrel hydrochloride according to the present invention is typically 0.7% or less, preferably 0.2% or less, more preferably 0.09% or less, still more preferably 0.07% or less, particularly preferably 0.05% or less.

The purity of the prasugrel hydrochloride, that is, the prasugrel content, can be measured as described for the OXTP content.

The purity of the high-purity prasugrel hydrochloride according to the present invention is typically 95% or more, preferably 97% or more, more preferably 99% or more.

Process for Producing High-Purity Free Prasugrel from Free Prasugrel This process is a process which involves dissolving free prasugrel in a solvent, followed by recrystallization to produce high-purity free prasugrel.

The solvent used in this process is not particularly limited, provided that it dissolves the starting material to a degree and does not inhibit the reaction. The solvent can be, for example, an aliphatic hydrocarbon such as hexane, cyclohexane, heptane, ligroin, or petroleum ether; an aromatic hydrocarbon such as benzene, toluene, or xylene; a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or diethylene glycol dimethyl ether; a ketone such as acetone, methyl ethyl ketone, or diethyl ketone; an ester such as ethyl acetate, propyl acetate, or butyl acetate; a carboxylic acid such as acetic acid or propionic acid; or a nitrile such as acetonitrile or propionitrile. Preferably, it is an ether, a ketone, an ester, a carboxylic acid, or a nitrile, more preferably tetrahydrofuran, dioxane, acetone, methyl ethyl ketone, ethyl acetate, acetic acid, or acetonitrile, particularly preferably tetrahydrofuran, acetic acid, acetone, or acetonitrile, most preferably acetonitrile.

The temperature during recrystallization is typically 20° C. to 80° C., preferably 30° C. to 70° C., more preferably 30° C. to 50° C. After dissolution, the solution is slowly cooled. It is preferred that a poor solvent (preferably water) is added thereto at −20° C. to −10° C., which is then stirred for 10 minutes to 3 hours. A seed crystal may also be added as needed.

The high-purity free prasugrel obtained in the process can be measured for the OXTP content using the following method.

The content of OXTP in the free prasugrel can be measured as described for the method of measuring the content of OXTP in the prasugrel hydrochloride.

The content of OXTP in the high-purity free prasugrel according to the present invention is typically 0.7% or less, preferably 0.2% or less, more preferably 0.09% or less, still more preferably 0.05% or less, particularly preferably 0.03% or less.

The purity of the free prasugrel, that is, the prasugrel content, can be measured as described for the OXTP content.

The purity of the high-purity free prasugrel according to the present invention is typically 95% or more, preferably 97% or more, more preferably 99% or more.

Process for Producing Acid Addition Salt of Prasugrel from High-Purity Free Prasugrel This process is a process which involves adding high-purity free prasugrel to an acid in an inert solvent or in the absence of a solvent (preferably in an inert solvent) or adding an acid optionally dropwise to high-purity free prasugrel in an inert solvent or in the absence of a solvent (preferably in an inert solvent) to produce an acid addition salt of prasugrel.

The acid used in the process can be, for example, an inorganic acid such as sulfuric acid, hydrochloric acid, nitric acid, or phosphoric acid; or an organic acid such as trifluoroacetic acid, maleic acid, methanesulfonic acid, benzenesulfonic acid, or p-toluenesulfonic acid. Preferably, it is hydrochloric acid, maleic acid, or benzenesulfonic acid, more preferably hydrochloric acid.

In this process, the adding of the acid optionally dropwise may be carried out by adding the acid dropwise or adding it at one time or in two to several divided portions.

The inert solvent used in this process is not particularly limited, provided that it dissolves the starting material to a degree and does not inhibit the reaction. The solvent can be, for example, an aliphatic hydrocarbon such as hexane, cyclohexane, heptane, ligroin, or petroleum ether; an aromatic hydrocarbon such as benzene, toluene, or xylene; a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or diethylene glycol dimethyl ether; a ketone such as acetone, methyl ethyl ketone, or diethyl ketone; an ester such as ethyl acetate, propyl acetate, or butyl acetate; a carboxylic acid such as acetic acid or propionic acid; or a nitrile such as acetonitrile or propionitrile. For the hydrochloride, is it preferably an ether, a ketone, an ester, a carboxylic acid, or a nitrile, more preferably tetrahydrofuran, dioxane, acetone, methyl ethyl ketone, ethyl acetate, acetic acid, or acetonitrile, particularly preferably tetrahydrofuran, dioxane, acetic acid, or acetone, most preferably acetone. For the maleate, on the other hand, it is preferably an ether, a ketone, an ester, or a nitrile, more preferably tetrahydrofuran, dioxane, acetone, methyl ethyl ketone, ethyl acetate, or acetonitrile, particularly preferably tetrahydrofuran, dioxane, or acetone, most preferably acetone.

The reaction temperature in the process varies depending on the reagent, solvent, or the like. However, it is typically −20° C. to 100° C., preferably 0° C. to 70° C., more preferably 30° C. to 60° C., most preferably 40° C. to 55° C.

The reaction time in the process varies depending on the reagent, solvent, reaction temperature, or the like. However, it is typically 5 minutes to 10 hours, preferably 10 minutes to 5 hours.

A preferred embodiment of a method for producing prasugrel maleate from high-purity free prasugrel is a method which involves dissolving maleic acid in acetone and adding high-purity free prasugrel thereto at 0° C. to 70° C. for reaction at the same temperature for 1 hour to 3 hours.

A preferred embodiment of a method for producing prasugrel hydrochloride from high-purity free prasugrel is a method which involves dissolving high-purity free prasugrel in acetone, adding dropwise half the necessary amount (typically, equimolar to the thienopyridine form) of concentrated hydrochloric acid thereto at 0° C. to 70° C. (preferably 35° C. to 60° C.) over a period of 2 minutes to 10 minutes, adding, if necessary, a seed crystal for reaction at the same temperature for 30 minutes to 2 hours, and further adding dropwise the remaining necessary amount of concentrated hydrochloric acid over a period of 30 minutes to 2 hours for reaction at 0° C. to 70° C. (preferably 25° C. to 55° C.) for 1 hour to 3 hours.

After the end of the reaction process, the acid addition salt of prasugrel of the present invention is collected from the reaction mixture according to a conventional method. For example, the desired compound is obtained by collecting the precipitated crystal by filtration after the end of the reaction or distilling off the solvent after the end of the reaction. The desired compound obtained may be, if necessary, further purified by a conventional method, for example, recrystallization, reprecipitation, or chromatography.

The high-purity prasugrel or an acid addition salt thereof obtained in the present invention is excellent in oral absorbability and metabolism-activating and platelet aggregation-inhibiting activity and weak in toxicity and further has good storage and handling stability, and therefore is useful as a medicine (preferably a prophylactic or therapeutic agent for diseases caused by thrombus or embolus (particularly, a therapeutic agent), more preferably a prophylactic or therapeutic agent for thrombosis or embolism (particularly, a therapeutic agent)). In addition, the medicine is preferably for use in warm-blooded animals, more preferably for use in humans.

When used as a therapeutic or prophylactic agent for diseases, the high-purity prasugrel or an acid addition salt thereof according to the present invention can be orally administered per se or in the form of tablets, capsules, granules, powders, syrups, or parenterally administered in the form of injections, suppositories, or the like in which a pharmacologically acceptable excipient, diluent or the like is mixed as needed.

These formulations are produced by well-known methods using additives including an excipient (which can be, for example, an organic excipient (e.g., a saccharide derivative such as lactose, sucrose, glucose, mannitol, or sorbitol; a starch derivative such as corn starch, potato starch, a pregelatinized starch, or dextrin; a cellulose derivative such as crystalline cellulose; gum arabic; dextran; or pullulan); or an inorganic excipient (e.g., light anhydrous silicic acid or a silicate derivative such as synthetic aluminum silicate, calcium silicate, or magnesium aluminometasilicate; a phosphate such as calcium hydrogenphosphate; a carbonate such as calcium carbonate; or a sulfate such as calcium sulfate)), a lubricant (which can be, for example, stearic acid or a metal stearate such as calcium stearate or magnesium stearate; talc; a wax such as beeswax or spermaceti; boric acid; adipic acid; a sulfate such as sodium sulfate; glycol; fumaric acid; sodium benzoate; D,L-leucine; a laurylsulfate such as sodium laurylsulfate or magnesium laurylsulfate; a silicic acid such as silicic anhydride or silicic acid hydrate; or a starch derivative as defined above), a binder (which can be, for example, hydroxypropylcellulose, hydroxypropyl methylcellulose, polyvinylpyrrolidone, polyethylene glycol, or a compound similar to an excipient as defined above), a disintegrant (which can be, for example, a cellulose derivative such as low substituted hydroxypropylcellulose, carboxymethylcellulose, carboxymethylcellulose calcium, or internally cross-linked carboxymethylcellulose sodium; a chemically modified starch/cellulose such as carboxymethyl starch, sodium carboxymethyl starch, or cross-linked polyvinylpyrrolidone; or a starch derivative as defined above), an emulsifier (which can be, for example, a colloidal clay such as bentonite or bee gum; a metal hydroxide such as magnesium hydroxide or aluminum hydroxide; an anionic surfactant such as sodium lauryl sulfate or calcium stearate; a cationic surfactant such as benzalkonium chloride; or a nonionic surfactant such as a polyoxyethylene alkyl ether, a polyoxyethylene sorbitan fatty acid ester, or a sucrose fatty acid ester), a stabilizer (which can be, for example, a p-hydroxybenzoic ester such as methylparaben or propylparaben; an alcohol such as chlorobutanol, benzyl alcohol, or phenylethyl alcohol; benzalkonium chloride; a phenol such as phenol, or cresol; thimerosal; dehydroacetic acid; or sorbic acid), a flavoring agent (such as, for example, a commonly used sweetener, acidulant or perfume), and a diluent.

The dosage of the high-purity prasugrel or an acid addition salt thereof according to the present invention can vary depending on various conditions such as the activity of the agent and the symptoms, age and weight of a patient. For oral administration, the dosages thereof can be each typically 0.01 mg/day/adult (preferably 1 mg/day/adult) as the lower limit and 200 mg/day/adult (preferably 100 mg/day/adult) as the upper limit.

EXAMPLES

The present invention is described below in further detail with reference to Examples, Reference Example, and Test Example. However, the invention is not intended to be limited thereto.

Example 1

Example of Production of High-purity Prasugrel Hydrochloride from Free Prasugrel To 8.00 g of 2-acetoxy-5-(α-cyclopropylcarbonyl-2-fluorobenzyl)-4,5,6,7-tetrahydrothieno[3,2-c]pyridine and 398 mg of activated clay was added 43 g of acetone, and the resulting mixture was then stirred at 32° C. The reaction solution was filtered, the residue was washed with 4.41 g of acetone, and then 1.12 g of 36% concentrated hydrochloric acid at 52° C. was added dropwise to the solution over a period of one minute. Thereto was added as a seed crystal 238 mg of crystal B2 obtained by the method described in JP2002-145883, and the resultant mixture was then stirred at the same temperature for one hour. In addition, 1.07 g of 36% concentrated hydrochloric acid was added dropwise thereto over a period of one hour, and the resultant mixture was then stirred at 40° C. for 2 hours and further at 30° C. for 1 hour. The precipitated crystal was collected by filtration, washed with 15.8 g of acetone, and dried under reduced pressure at 50° C. for 5 hours to provide 8.01 g of the title compound.

Liquid chromatography of the resultant high-purity prasugrel hydrochloride is shown in FIG. 5.

Measurement conditions in FIG. 5 are as follows.

(Measurement Conditions) Detector: ultraviolet absorptiometer (measuring wavelength; 240 nm)

Analytical Column: Cadenza CD-C18, inner diameter; 4.6 mm, length; 15 cm, particle size; 3 μm Guard Column: none Column Temperature: 40° C.

Mobile Phase: 0.01 mol/L potassium dihydrogenphosphate aqueous solution:tetrahydrofuran:acetonitrile=13:5:2 (V/V/V)

Flow Rate: 1.0 mL/min.

Example 2

Example of Production of High-purity Free Prasugrel from Free Prasugrel

To 7.00 g of the compound (I) was added 46.3 g of acetonitrile, and the resultant mixture was then stirred at 40° C. for 10 minutes, followed by cooling the reaction solution to −15° C. Thereto was added dropwise 29.4 g of water precooled to the same temperature over a period of 35 minutes, and the resultant mixture was then stirred at the same temperature for 30 minutes. The precipitated crystal was collected by filtration, washed with 10.5 g of a precooled acetonitrile-water mixed solvent, and dried under reduced pressure at 45° C. for 5 hours to provide 6.50 g of the title compound.

Liquid chromatography of the resultant high-purity free prasugrel is shown in FIG. 6.

Measurement conditions in FIG. 6 are as follows.

(Measurement Conditions) Detector: ultraviolet absorptiometer (measuring wavelength; 240 nm)

Analytical Column: Cadenza CD-C18, inner diameter; 4.6 mm, length; 15 cm, particle size; 3 μm Guard Column: none Column Temperature: 40° C.

Mobile Phase: 0.01 mol/L potassium dihydrogenphosphate aqueous solution:tetrahydrofuran:acetonitrile=13:5:2 (V/V/V)

Flow Rate: 1.0 mL/min.

Reference Example 1

2-Acetoxy-5-(α-cyclopropylcarbonyl-2-fluorobenzyl)-4,5,6,7-tetrahydrothieno[3,2-c]pyridine (1) 2-Fluoro-α-cyclopropylcarbonylbenzyl chloride A mixture of 100 g of cyclopropyl 2-fluorobenzyl ketone and 886 g of dichloromethane was stirred while cooling with ice to provide a mixed solution. Into the resultant mixed solution was blown 3.98 g (0.1 equivalent) of chlorine gas over a period of 20 minutes while keeping the solution temperature at 0° C., and the resultant mixture was then stirred for 0.5 hour while maintaining the solution temperature at 0° C. Further, 39.8 g (1 equivalent) of chlorine gas was blown thereinto over a period of 220 minutes while keeping the solution temperature at 0° C., which was reacted by stirring for one hour while maintaining the solution temperature at 0° C.

After the end of the reaction, 236 g of a 3% sodium thiosulfate aqueous solution was added dropwise to the resultant reaction solution under stirring while keeping the solution temperature at not more than 15° C. After the dropwise addition, the solution was stirred for 10 minutes and then subjected to a liquid-separating operation. The resultant organic layer was washed with 589 g of a precooled 8% sodium hydrogencarbonate aqueous solution and then with 168 g of precooled water and concentrated under reduced pressure to provide 145 g of the title compound in an oily form (pure content: 95.4 g, yield: 80%).

(2) 2-(tert-Butyldimethylsilyloxy)-5-(α-cyclopropylcarbonyl-2-fluorobenzyl)-4,5,6,7-tetrahydrothieno[3,2-c]pyridine To a mixture of 115 g of 5,6,7,7a-tetrahydro-4H-thieno[3,2-c]pyridine-2-one p-toluenesulfonate, 60.7 g of tert-butyldimethylchlorosilane, and 277 g of dichloromethane was added 40.7 g of triethylamine, and the resultant mixture was then stirred at 25° C. for one hour to provide a mixed solution. To the mixed solution were added 78.1 g of the 2-fluoro-α-cyclopropylcarbonylbenzyl chloride obtained in (1), 70.8 g of triethylamine, and 1.57 g of sodium iodide, which was then reacted by stirring at 45° C. for one hour and further at 52° C. for 5 hours.

After the end of the reaction, to the resultant reaction solution was added the entire amount of a phosphate buffer solution prepared by adding distilled water to 9.50 g of $KH_2PO_4$ and 0.95 g of $Na_2HPO_4.12H_2O$ into a total weight of 358 g, which was then subjected to a liquid-separating operation, followed by subjecting the aqueous layer to back extraction with 116 g of dichloromethane. The resultant organic layers were combined and concentrated under reduced pressure until the residue reached a volume of 218 mL. Thereto was added 476 g of acetonitrile, and the resultant mixture was then concentrated under reduced pressure until the residue reached a volume of 517 mL. To the resultant residue was added 238 g of acetonitrile, and the resultant mixture was then stirred at 30° C. for 30 minutes. Subsequently, 122 g of water was added thereto, and the resultant mixture was then stirred at 0° C. for 3 hours. The precipitated crystal was collected by filtration, washed with 69.0 g of precooled acetonitrile, and dried under reduced pressure to provide 131 g of a crude material of the title compound.

To 40.0 g of the crude material was added 252 g of acetonitrile, which was stirred at 50° C. for 10 minutes and then cooled to 30° C. Subsequently, 40 g of water was added dropwise thereto at the same temperature over a period of 30 minutes, and the resultant mixture was then cooled to 0° C. and stirred at the same temperature for 3 hours. The precipitated crystal was collected by filtration, washed with 30 g of precooled acetonitrile, and dried under reduced pressure to provide 37.6 g of the title compound.

(3) 2-Acetoxy-5-(α-cyclopropylcarbonyl-2-fluorobenzyl)-4,5,6,7-tetrahydrothieno[3,2-c]pyridine A mixed solution of 6.20 g of acetic anhydride and 5.90 g of acetonitrile was added dropwise to the mixture of 22.5 g of 2-(tert-butyldimethylsilyloxy)-5-α-cyclopropylcarbonyl-2-fluorobenzyl)-4,5,6,7-tetrahydrothieno[3,2-c]pyridine obtained in (2), 7.65 g of triethylamine, 62.0 mg of 4-dimethylaminopyridine, and 113 g of acetonitrile, and the reaction was performed by stirring at −15° C. for one hour.

After the end of the reaction, 75.9 g of cold water was added to the resultant reaction solution, and the resultant mixture was then stirred at −10° C. for 30 minutes. The precipitated crystal was collected by filtration, washed with a mixture of 22.7 g of precooled acetonitrile and 17.8 g of cold water, and dried under reduced pressure to provide 16.4 g of the title compound.

Test Example 1

Preparation of Impurity OXTP Standard

OXTP can be produced, for example, by the method described in Example 20 of Japanese Patent Laid-Open No. 06-41139.

Method for Measuring Prasugrel Content and OXTP Content in Prasugrel Hydrochloride or Free Prasugrel The content of prasugrel in free prasugrel or the hydrochloride thereof was measured as described below.

In an acetonitrile-water mixed solution (7:3) was dissolved 150 mg of free prasugrel or the hydrochloride thereof to 100 mL. 10 µL of the solution was subjected to liquid chromatography for measurement under the following conditions.

Measurement Conditions (Liquid Chromatography)

(Measurement Conditions) Detector: ultraviolet absorptiometer (measuring wavelength; 240 nm)

Analytical Column: Cadenza CD-C18, inner diameter; 4.6 mm, length; 15 cm, particle size; 3 µm Guard Column: none Column Temperature: 40° C.

Mobile Phase: 0.01 mol/L potassium dihydrogenphosphate aqueous solution:tetrahydrofuran:acetonitrile=13:5:2 (V/V/V)

Flow Rate: 1.0 mL/min.

TABLE 1

(Measurements of prasugrel and OXTP contents in prasugrel hydrochloride or free prasugrel)

| | Purities in prasugrel hydrochloride or free prasugrel | |
|---|---|---|
| | Prasugrel content (%) | OXTP content (%) |
| Starting material of Example 1 (Free prasugrel) | 99.513 | 0.095 |
| Product of Example 1 (Prasugrel hydrochloride) | 99.690 | 0.032 |
| Starting material of Example 2 (Free prasugrel) | 99.513 | 0.095 |
| Product of Example 2 (Free prasugrel) | 99.711 | 0.014 |

The prasugrel hydrochloride of Example 1 produced by the reaction of free prasugrel containing OXTP with hydrochloric acid had a reduced content of OXTP, indicating that high-purity prasugrel hydrochloride had been successfully produced. The free prasugrel of Example 2 produced by the recrystallization of free prasugrel containing OXTP had a further reduced content of OXTP, indicating that high-purity free prasugrel had been successfully produced.

Industrial Applicability

According to the present invention, there are obtained high-purity prasugrel and an acid addition salt (particularly, hydrochloride) thereof with a reduced content of impurities such as the by-product OXTP.

BRIEF DESCRIPTION OF THE DRAWINGS

FIG. 1 is a powder X-ray diffraction pattern for crystal A of prasugrel hydrochloride, obtained by irradiation with copper Kα radiation (wavelength λ 1.54 angstroms). In the powder X-ray diffraction pattern, the ordinate axis represents diffraction intensity in counts/second (cps) and the horizontal axis represents the diffraction angle 2θ in degrees;

FIG. 2 is a powder X-ray diffraction pattern for crystal B1 of prasugrel hydrochloride, obtained by irradiation with copper Kα radiation (wavelength λ=1.54 angstroms). In the powder X-ray diffraction pattern, the ordinate axis represents diffraction intensity in counts/second-(cps) and the horizontal axis represents the diffraction angle 2θ in degrees;

FIG. 3 is a powder X-ray diffraction pattern for crystal B2 of prasugrel hydrochloride, obtained by irradiation with copper Kα radiation (wavelength λ=1.54 angstroms). In the powder X-ray diffraction pattern, the ordinate axis represents diffraction intensity in counts/second (cps) and the horizontal axis represents the diffraction angle 2θ in degrees;

FIG. 4 is a powder X-ray diffraction pattern for a crystal of free prasugrel, obtained by irradiation with copper Kα radiation (wavelength λ=1.54 angstroms). In the powder X-ray diffraction pattern, the ordinate axis represents diffraction intensity in counts/second (cps) and the horizontal axis represents the diffraction angle 2θ in degrees;

FIG. 5 is the result of the liquid chromatography of prasugrel hydrochloride obtained in Example 1; and FIG. 6 is the result of the liquid chromatography of free prasugrel obtained in Example 2.

The invention claimed is:

1. A method for producing prasugrel hydrochloride of the formula:

Formula 2

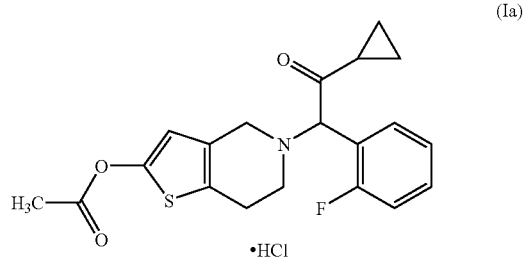

(Ia)

with a reduced content of OXTP, comprising preparing free prasugrel of the formula:

Formula 1

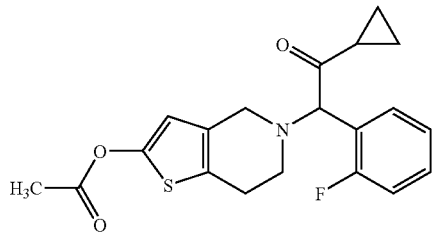

(I)

containing OXTP;

dissolving the free prasugrel represented by the formula (I) in an inert solvent, and adding hydrochloric acid optionally dropwise to the solution;

wherein the method of preparing free prasugrel comprises the steps of:
(i) chlorinating cyclopropyl 2-fluorobenzylketone by blowing chlorine gas thereto in dichloromethane while keeping the solution temperature at 0° C. and stirring at same temperature to synthesize 2-fluoro-α-cyclopropylcarbonylbenzylchloride;
(ii) reacting 2-fluoro-α-cyclopropylcarbonylbenzyl-chloride with the product, which is obtained from reacting 5,6,7,7a-tetrahydro-4H-thieno[3,2-c]pyridine-2-on p-toluenesulfonate and tert-butyldimethyl-chlorosilane in dichloromethane in the presence of triethylamine and sodium iodide to synthesize 2-(tert-butyldimethylsilyloxy)-5-(α-cyclopropylcarbonyl-2-fluorobenzyl)-4,5,6,7-tetrahydrothieno[3,2-c]pyridine, and recrystallizing thereof;
(iii) acetylating 2-(tert-butyldimethylsilyloxy)-5-(α-cyclopropylcarbonyl-2-fluorobenzyl)-4,5,6,7-tetrahydrothieno[3,2-c]pyridine by reacting acetic anhydride therewith in acetonitrile in the presence of triethylamine and 4-dimethylaminopyridine at −15° C.

2. A method for producing prasugrel hydrochloride according to claim 1, wherein the inert solvent is acetone.

* * * * *